US012605125B2

(12) United States Patent
Hofmann et al.

(10) Patent No.: US 12,605,125 B2
(45) Date of Patent: Apr. 21, 2026

(54) RADIOTHERAPY SYSTEM WITH INTEGRATED STATIC COMPUTED TOMOGRAPHY IMAGING

(71) Applicant: SIEMENS HEALTHINEERS INTERNATIONAL AG, Palo Alto, CA (US)

(72) Inventors: Christian Hofmann, Erlangen (DE); Patrick Wohlfahrt, Erlangen (DE); Christian Möhler, Karlsruhe (DE)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 432 days.

(21) Appl. No.: 18/199,350

(22) Filed: May 18, 2023

(65) Prior Publication Data

US 2024/0130694 A1 Apr. 25, 2024
US 2024/0225566 A9 Jul. 11, 2024

Related U.S. Application Data

(60) Provisional application No. 63/418,026, filed on Oct. 20, 2022.

(51) Int. Cl.
*A61B 6/03* (2006.01)
*A61B 6/40* (2024.01)
(Continued)

(52) U.S. Cl.
CPC ............ *A61B 6/032* (2013.01); *A61B 6/4007* (2013.01); *A61B 6/4078* (2013.01);
(Continued)

(58) Field of Classification Search
CPC .................... A61N 5/1049; A61N 5/10; A61N 2005/1061; A61N 2005/1048;
(Continued)

(56) References Cited

U.S. PATENT DOCUMENTS

2011/0210261 A1 9/2011 Maurer, Jr.
2011/0211665 A1* 9/2011 Maurer, Jr. .......... A61N 5/1039
378/19

(Continued)

OTHER PUBLICATIONS

International Search Report and Written Opinion of the International Searching Authority, International application No. PCT/EP2023/077623, Dec. 19, 2023.

*Primary Examiner* — Don K Wong
(74) *Attorney, Agent, or Firm* — SU IP CONSULTING

(57) ABSTRACT

A radiation treatment system includes a radiation delivery system including a rotatable gantry that is coupled to a static portion of the radiation treatment system and a radiation source that directs treatment radiation to a target volume and is mounted on the rotatable gantry for rotation about the target volume. The radiation treatment system further includes a computed tomography (CT) imaging system that generates portions of a CT scan of a region of patient anatomy that includes the target volume, wherein the CT imaging system includes an arcuate array of x-ray detectors, and an array of x-ray sources positioned around the target volume, wherein each x-ray source in the array of x-ray sources is oriented to direct imaging x-rays towards a different portion of the arcuate array of x-ray detectors.

21 Claims, 13 Drawing Sheets

(51) Int. Cl.
*A61B 6/42* (2024.01)
*A61N 5/10* (2006.01)

(52) U.S. Cl.
CPC .......... *A61B 6/4233* (2013.01); *A61B 6/4266* (2013.01); *A61B 6/4275* (2013.01); *A61N 5/1081* (2013.01)

(58) Field of Classification Search
CPC ................ A61N 5/1082; A61N 5/1048; A61N 2005/1062; A61N 5/103
See application file for complete search history.

(56) References Cited

U.S. PATENT DOCUMENTS

| 2012/0008734 | A1 | 1/2012 | Thomson et al. |
| 2022/0203134 | A1 | 6/2022 | Givehchi et al. |

* cited by examiner

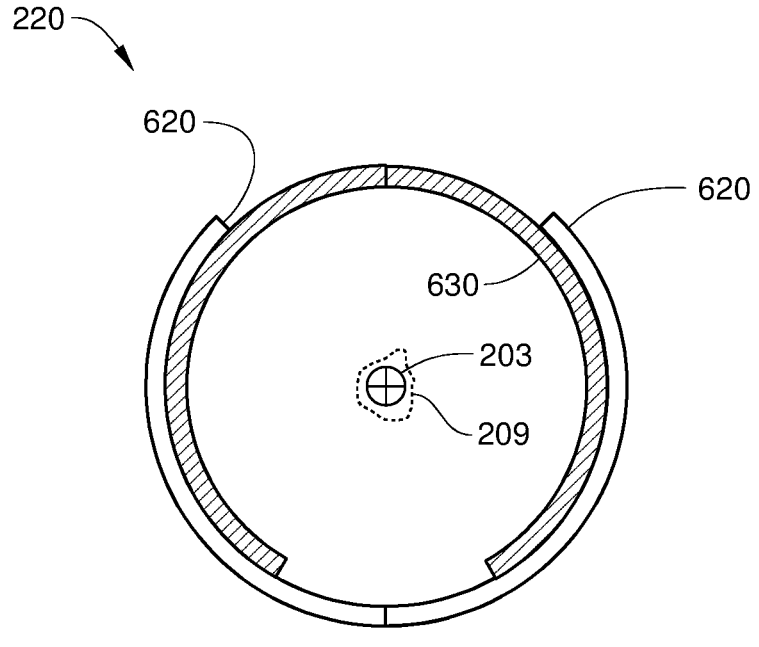
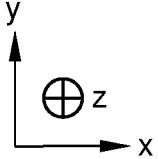
FIG. 6

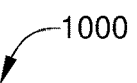
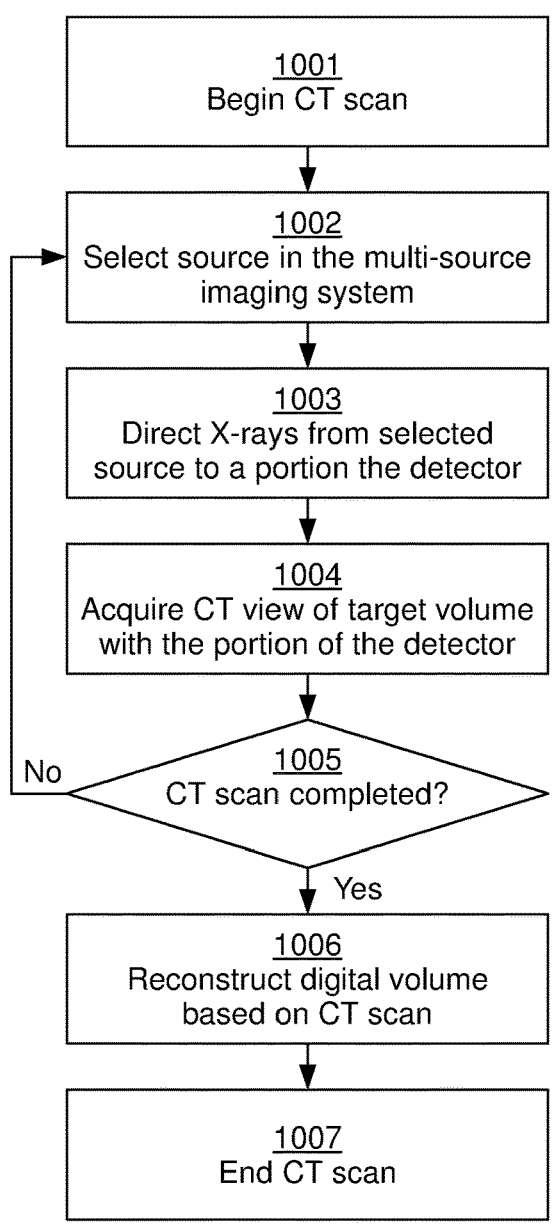
1001
Begin CT scan
1002
Select source in the multi-source imaging system
1003
Direct X-rays from selected source to a portion the detector
1004
Acquire CT view of target volume with the portion of the detector
1005
CT scan completed?
No
Yes
1006
Reconstruct digital volume based on CT scan
1007
End CT scan
FIG. 10

RADIOTHERAPY SYSTEM WITH INTEGRATED STATIC COMPUTED TOMOGRAPHY IMAGING

CROSS-REFERENCE TO RELATED APPLICATION

The present application claims the benefit of U.S. Provisional Application 63/418,026 filed on Oct. 20, 2022. The provisional application is hereby incorporated by reference in its entirety.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy that is performed on the planning target volume spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area, referred to as the "treatment planning image." From such imaging, the size and mass of the target tissue can be estimated, a planning target volume determined, and an appropriate treatment plan generated. Generally, treatment planning based on computed tomography (CT) is the current gold standard, and thus a CT scan for patient simulation represents the starting point for organ and tumor segmentation as well as dose calculation.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image-guided radiation therapy (IGRT), and involves the use of an imaging system to view target tissues immediately before, or sometimes while, radiation treatment is delivered to the planning target volume.

IGRT incorporates imaging coordinates from the treatment plan to ensure the patient is properly aligned for treatment in the radiation therapy device, thereby enabling an increase in accuracy and precision of treatment delivery, shorter treatment times (e.g., hypo-fractionated therapy and/or flash therapy), and patient-individualized therapy. Using IGRT, an adaptive therapy workflow with plan adaptation ("plan of the day") can be performed, which is based on the actual patient anatomy on the day of treatment. For instance, during a course of radiotherapy, which can take place over many days, the planning target volume and/or neighboring patient anatomy can change in size or relative position due to tumor shrinkage, patient weight loss, variation in bowel or bladder content, and the like. An adaptive therapy workflow, such as adaptive radiotherapy (ART), can take into account additional information gained about patient anatomy via day-of-treatment imaging for each treatment fraction. Adaptive radiotherapy enables the treatment to be changed, or adapted, to respond to such additional information indicating that patient anatomy has changed relative to the original state of the anatomy at the time of planning. Thus, IGRT can oftentimes meet the demands of high-precision radiotherapy that attempts to provide treatment with improved tumor control, patient comfort, and reduced toxicity.

SUMMARY

According to various embodiments, a radiation therapy system includes a radiation delivery system for directing treatment radiation to a target volume and a CT imaging system for generating CT scans of patient anatomy surrounding the target volume. In the embodiments, the CT imaging system includes an arcuate array of x-ray detectors positioned around the target volume and an array of x-ray sources positioned around the target volume. In operation, the radiation delivery system and the CT imaging system are rotated about a treatment isocenter via a rotatable gantry at a relatively low rotational velocity as a treatment beam is directed to the treatment isocenter. For example, the rotatable gantry may rotate on the order of 5-10 seconds per rotation during treatment delivery. Simultaneously, the CT imaging system generates one or more CT scans at a rate of more than one per second. Each CT scan includes the sub-second acquisition of a plurality of CT views across an image acquisition arc of up to 360 degrees about the treatment isocenter. The sub-second acquisition of the CT slices is completed by sequentially generating each CT view with a different x-ray source in the array of x-ray sources. The CT scans so generated provide the sub-second temporal resolution and high soft tissue contrast of a conventional CT scanner. As a result, intra-fraction motion can be detected in real-time, for example in one-half second or less.

In some embodiments, a computer-implemented method of imaging a target volume in a patient anatomy includes: selecting a first source in an array of x-ray sources that are positioned around the target volume; acquiring a first portion of a computed tomography (CT) scan with a first portion of a detector array that receives imaging x-rays from the first source in the array of x-ray sources; after acquiring the first portion of the CT scan: selecting a second source in the array of x-ray sources; and acquiring a second portion of the CT scan with a second portion of the detector array that receives imaging x-rays from the second source in the array of x-ray sources; and based on the first portion of the CT scan and the second portion of the CT scan, reconstructing a digital volume of a region of patient anatomy that includes the target volume.

In some embodiments, a radiation treatment system includes: a radiation delivery system that includes: a rotatable gantry that is coupled to a static portion of the radiation treatment system; and a radiation source that directs treatment radiation to a target volume and is mounted on the rotatable gantry for rotation about the target volume. The radiation treatment system further includes: a computed tomography (CT) imaging system that generates portions of a CT scan of a region of patient anatomy that includes the target volume, wherein the CT imaging system includes: an arcuate array of x-ray detectors; and an array of x-ray sources positioned around the target volume, wherein each x-ray source in the array of x-ray sources is oriented to direct imaging x-rays towards a different portion of the arcuate array of x-ray detectors.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

FIG. 6 is a schematic axial view of a CT imaging system, according to an embodiment.

FIG. 10 sets forth a flowchart of a computer-implemented process for performing a CT scan of a region of patient anatomy, according to various embodiments.

DETAILED DESCRIPTION

Figure 1:
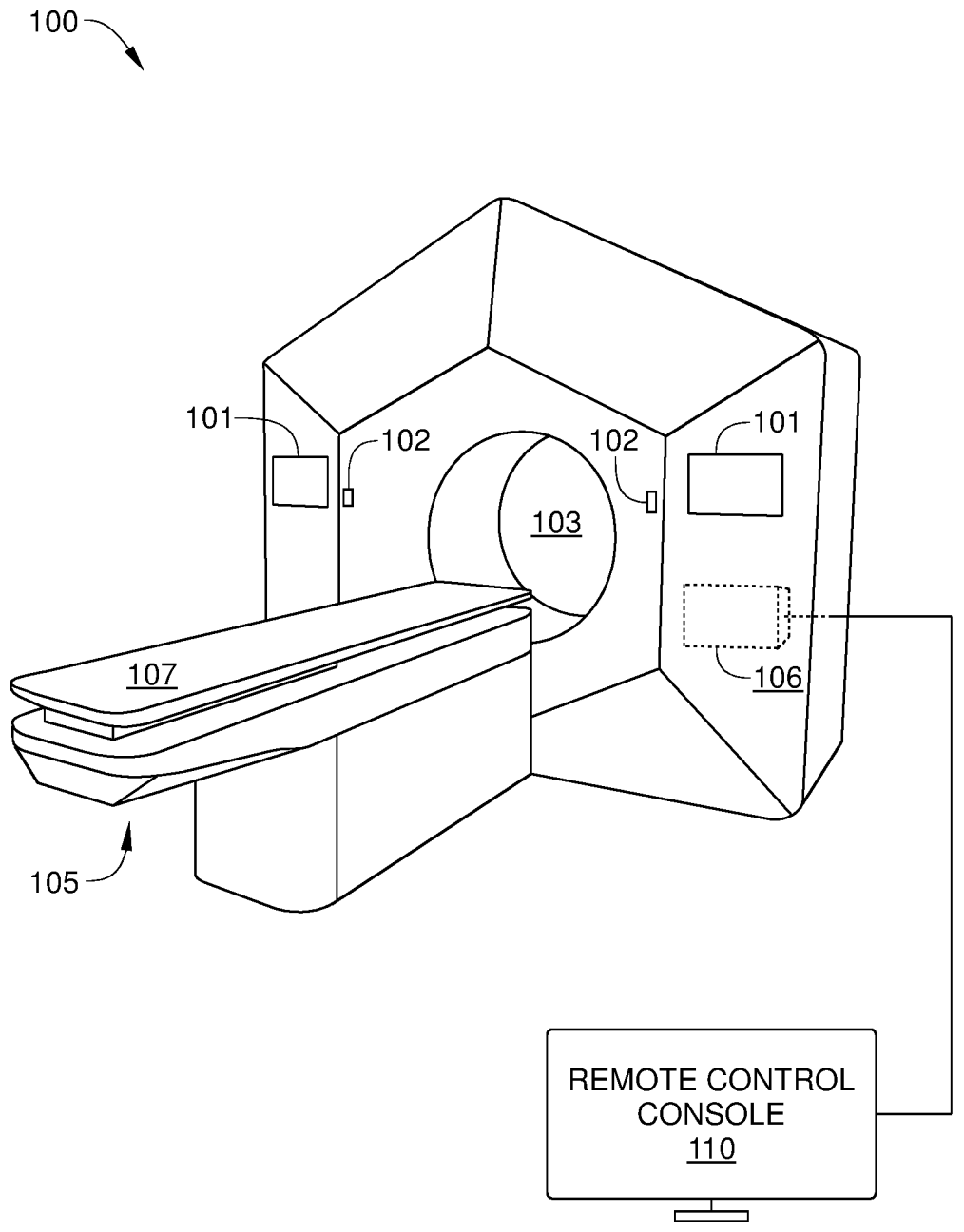
FIG. 1 is a perspective view of a CT linear accelerator (LINAC) system, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

INTRODUCTION

As noted previously, image-guided radiation therapy (IGRT) and adaptive therapy workflows have been developed to take into account additional information gained about patient anatomy via day-of-treatment imaging for each treatment fraction. In addition, patient imaging during a particular treatment fraction can be performed to detect intra-fraction motion during radiation treatment, such as anatomical variations occurring due to peristalsis, gas bubble motion, loss of breath hold, and the like. However, conventional IGRT often cannot compensate for the structural and spatial changes that can occur in patient anatomy during a particular treatment session. This is because conventional onboard x-ray imaging for radiation therapy systems is incapable of imaging patient anatomy with sufficiently high temporal resolution (e.g., <0.5 seconds) and soft tissue contrast to enable verification and tracking of patient anatomy or steering dose delivery during treatment.

In conventional radiation therapy systems, onboard imaging is limited to acquiring cone-beam computed tomography (CBCT) projection images with an x-ray imaging system that is rotated about the treatment isocenter at the same rotational velocity as the linear accelerator (LINAC) that generates the treatment radiation. Since the LINAC is typically rotated slowly about the treatment isocenter during treatment delivery (e.g., one complete rotation in 5-10 seconds), the x-ray imaging system can only acquire CBCT projection images across a very limited arc over a time interval that can provide sub-second temporal resolution. Further, reconstructions based on CBCT images are subject to more image artifacts than those based on computed tomography (CT) scans, such as noise, metal artifacts, and motion artifacts. Image artifacts contribute to image degradation, and modifying treatment delivery in real-time based on degraded images can lead to inaccurate dosing. Therefore, the use of onboard CBCT imaging systems for providing imaging of patient anatomy with real-time (i.e., sub-second) temporal resolution is problematic.

Ideally, the above problem could be addressed by using a conventional CT scanner for the onboard imaging of a radiation therapy system. However, such a solution requires a first mechanical system (a LINAC) that rotates relatively slowly about the treatment isocenter with a second mechanical system (the CT x-ray source and detector) that rotates many times faster. The integration and operation of such a system is an extremely complex mechanical problem. In addition, because the CT x-ray source and detector must rotate around the treatment isocenter faster than the LINAC, the CT x-ray source and detector will repeatedly occlude the treatment beam produced by the LI NAC during treatment. Consequently, the implementation of a conventional CT scanner as onboard imaging for radiation therapy systems is generally considered unworkable.

In light of the above, there is a need in the art for improved techniques for imaging patient anatomy in LINAC-based radiation therapy systems.

According to various embodiments, a radiation therapy system includes a distributed-source CT scanning system that is rotated about the treatment isocenter along with the LINAC and generates CT scans of patient anatomy with sub-second temporal resolution and high soft tissue contrast of a conventional CT scanner. As a result, intra-fraction motion can be detected in real-time, for example in one-half second or less. Thus, the radiation therapy system can perform image-guided radiation therapy (IGRT) that monitors intra-fraction motion using CT-quality X-ray imaging, rather than CBCT imaging or magnetic resonance imaging (MRI). Detected anatomical variations can then either be compensated for, via patient repositioning and/or treatment modification, or the current treatment can be aborted.

System Overview

FIG. 1 is a perspective view of a CT LINAC 100, according to various embodiments. CT LINAC 100 is a radiation therapy system that includes a radiation delivery system for generating a treatment beam, such as a LINAC, and a CT imaging system for performing CT scans of patient anatomy. In the embodiments, the CT imaging system can perform the CT scans before and/or during delivery of the treatment beam. Further, the CT scans so performed can have the temporal resolution and high soft tissue contrast of conventional CT scans. Since CT LI NAC 100 can complete a CT scan in less than 1 second or even less than one half second, such CT scans can be employed to detect intra-fraction motion in real time. Thus, CT LI NAC 100 can provide precision radiotherapy for lesions, tumors, and conditions anywhere in the body where radiation treatment is indicated, such as stereotactic radiosurgery. As such, CT LINAC 100 can include a linear accelerator (LINAC) that generates a megavolt (MV) treatment beam of high energy x-rays, a distributed-source CT scanning system (not visible in FIG. 1), and, in some embodiments, an MV electronic portal imaging device (EPID). By way of example, CT LINAC 100 is described herein configured with a circular gantry. In other embodiments, CT LINAC 100 can be configured with a C-gantry capable of infinite rotation via a slip ring connection.

In the embodiment illustrated in FIG. 1, CT LINAC 100 is capable of CT x-ray imaging of a target volume immediately prior to and/or during application of an MV treatment beam, so that an IGRT and/or an intensity-modulated radiation therapy (IMRT) process can be performed using CT x-ray imaging. CT LINAC 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. CT LINAC 100 further includes a remote control console 110, which is disposed outside the treatment room and enables treatment delivery and patient monitoring from a remote location. Base positioning assembly 105 is configured to precisely position couch 107 with respect to bore 103. Motion controls 102 include input devices, such as button and/or switches, that enable a user to operate base positioning assembly 105 to automatically position couch 107 to a predetermined location with respect to bore 103. Motion controls 102 also enable a user to manually position couch 107 to a predetermined location.

Figure 2:
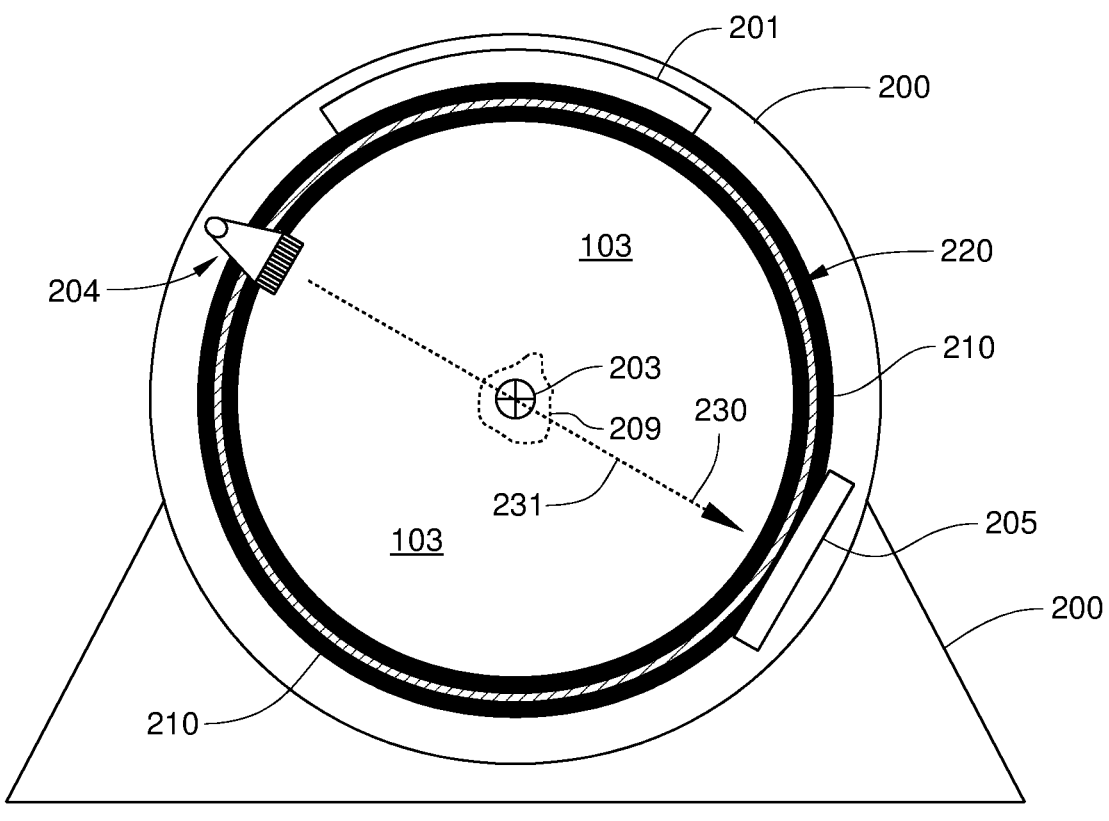
FIG. 2 schematically illustrates a drive stand and rotatable gantry of the CT LINAC system of FIG. 1, according to various embodiments.

FIG. 2 schematically illustrates a drive stand 200 and rotatable gantry 210 (solid black) of CT LINAC 100, according to various embodiments. Covers, base positioning assembly 105, couch 107, and other components of CT LINAC 100 are omitted in FIG. 2 for clarity. Drive stand 200 is a fixed support structure for components of CT LINAC 100, including rotatable gantry 210 and a drive system 201 for rotatably moving rotatable gantry 210. Drive stand 200 rests on and/or is fixed to a support surface that is external to CT LINAC 100, such as a floor of an radiotherapy treatment facility. Rotatable gantry 210 is rotationally coupled to drive stand 200 and is a support structure on which various components of CT LINAC 100 are mounted, including a linear accelerator (LINAC) 204 (or other treatment beam source), an MV electronic portal imaging device (EPID) 205, and a CT imaging system 220 (cross-hatched). During operation of CT LINAC 100, gantry 220 rotates about bore 103 when actuated by drive system 201, simultaneously rotating LINAC 204 and CT imaging system 220 about a treatment isocenter 203.

Drive system 201 rotationally actuates rotatable gantry 210. In some embodiments, drive system 201 includes a linear motor that can be fixed to drive stand 200 and interacts with a magnetic track (not shown) mounted on rotatable gantry 210. In other embodiments, drive system 201 includes another suitable drive mechanism for precisely rotating rotatable gantry 210 about bore 201. LINAC 204 generates an MV treatment beam 230 of high energy x-rays (or in some embodiments electrons, protons, and/or other heavy charged particles, ultra-high dose rate x-rays (e.g., for FLASH radiotherapy) or microbeams for microbeam radiation therapy). EPID 205 is configured to acquire x-ray images with treatment beam 230. CT imaging system 220 is configured to acquire CT scans of a region of patient anatomy that includes treatment isocenter 203. Specifically, CT imaging system 220 includes a distributed source assembly and an x-ray imager. The distributed source assembly includes a plurality of x-ray sources, each of which is positioned to direct imaging x-rays through a region of patient anatomy that includes a target volume 209 and towards a different portion of the x-ray imager. Target volume 209 is a portion of patient anatomy to be treated with treatment beam 230 and is typically colocated with treatment isocenter 203. In operation, a different CT view of the region of patient anatomy is acquired for each x-ray source of the distributed source assembly, and these CT views are used to reconstruct imaging data for a digital volume of patient anatomy within a 3D region that includes target volume 209. One embodiment of such a digital volume is described below in conjunction with FIG. 3, and various embodiments of CT imaging system 220 are described below in conjunction with FIGS. 4A-9B.

Figure 3:
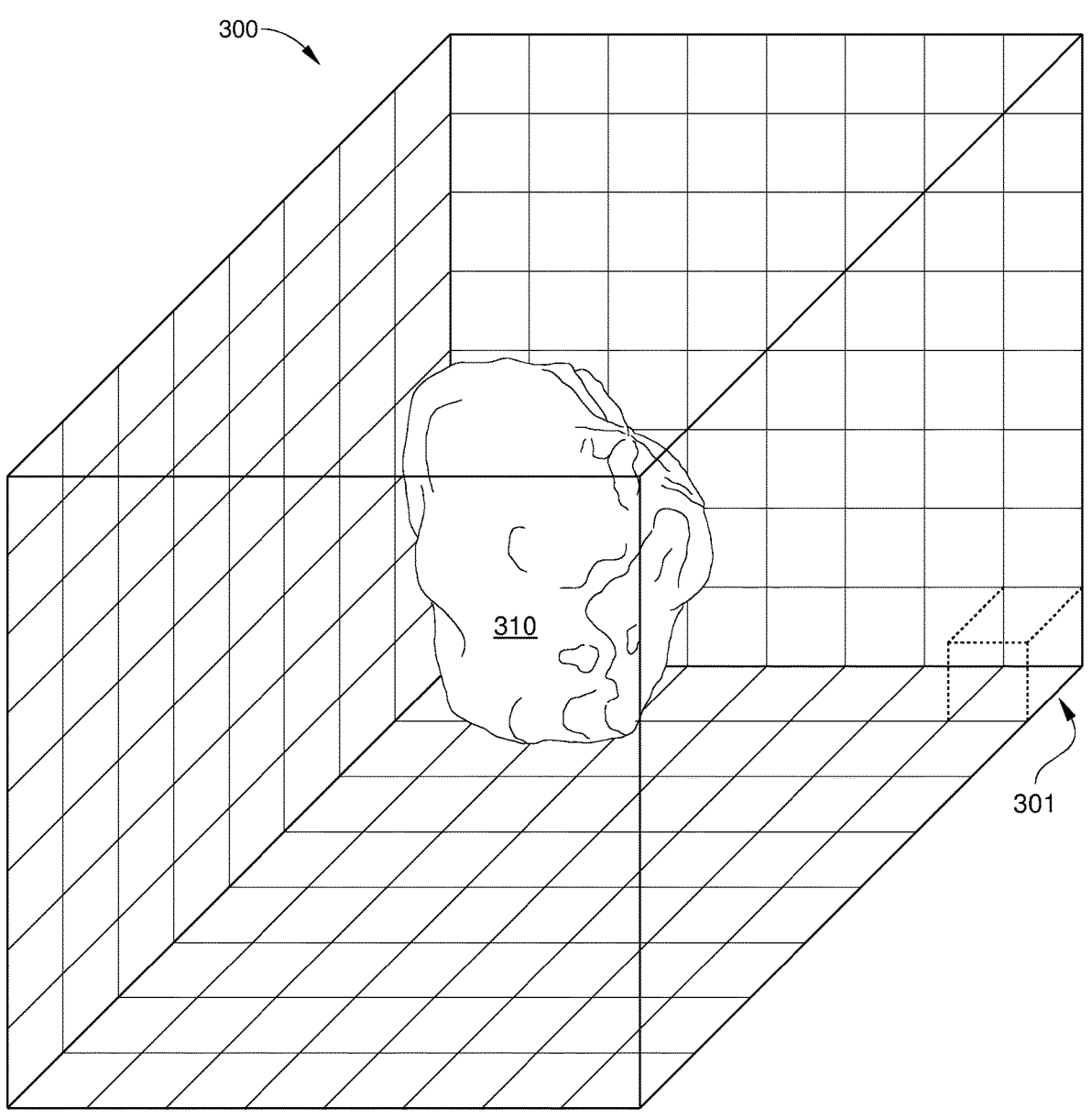
FIG. 3 schematically illustrates a digital volume that is reconstructed based on a plurality of CT views acquired by the CT imaging system of FIG. 2, according to various embodiments.
Figure 4:
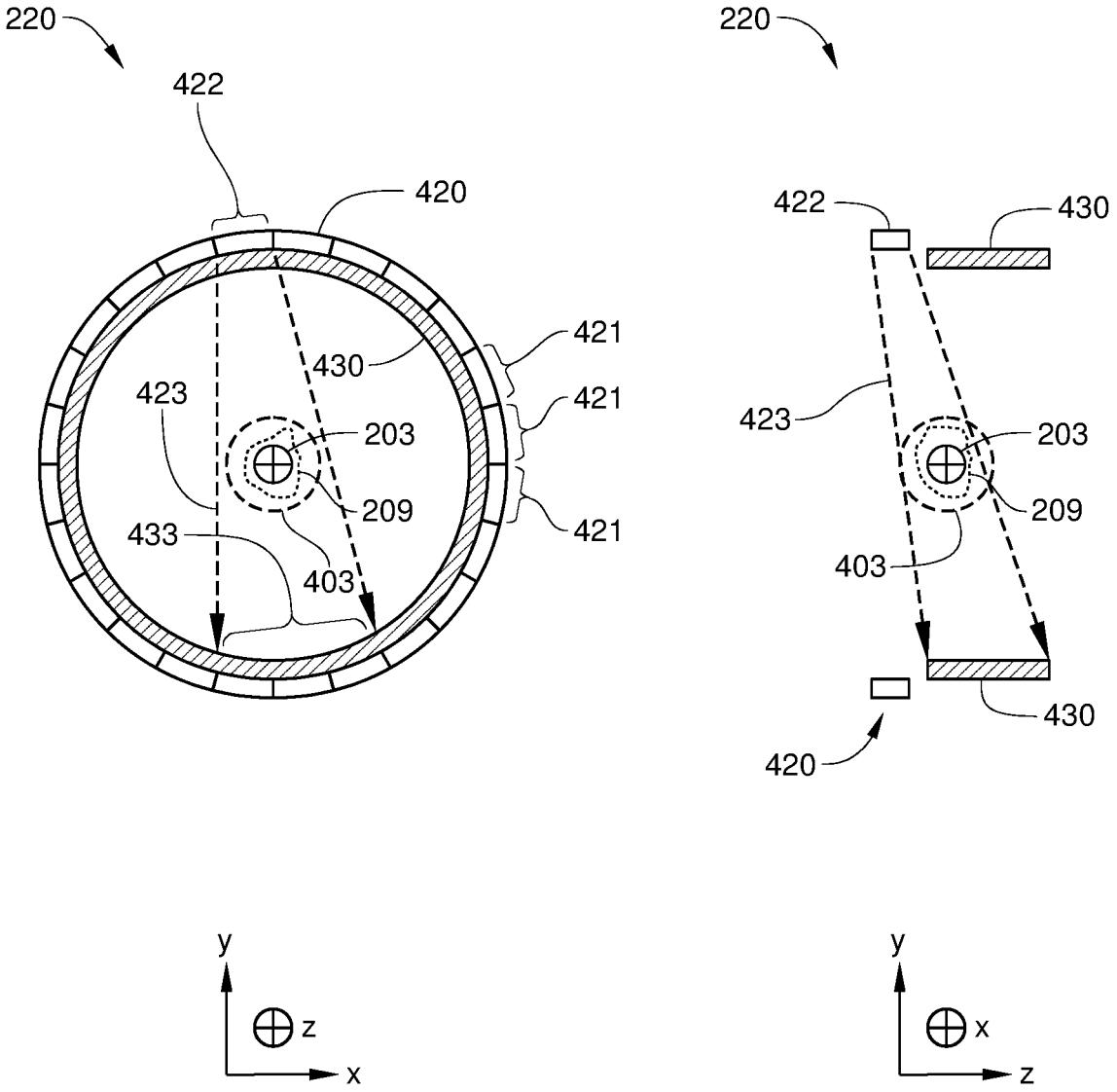
FIG. 4A is a schematic axial view of a CT imaging system and FIG. 4B is a schematic side view of the CT imaging system, according to an embodiment.
Figure 5:
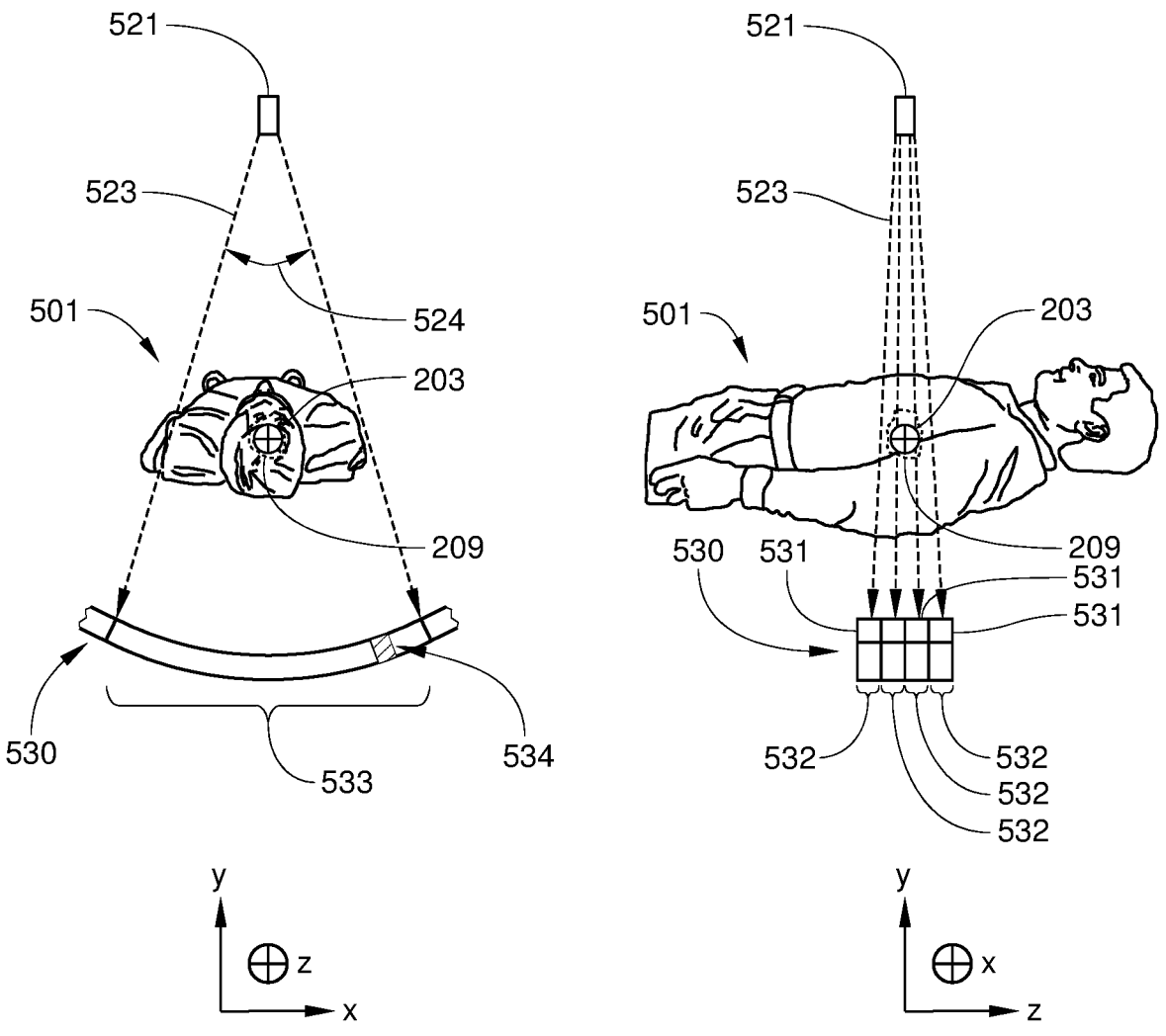
FIG. 5A is a schematic axial view of a single x-ray source directing imaging x-rays towards a specific portion of an arcuate x-ray imager and FIG. 5B is a schematic side view of the x-ray source directing the imaging x-rays towards the specific portion of the arcuate X-ray imager, according to an embodiment.
Figure 7:
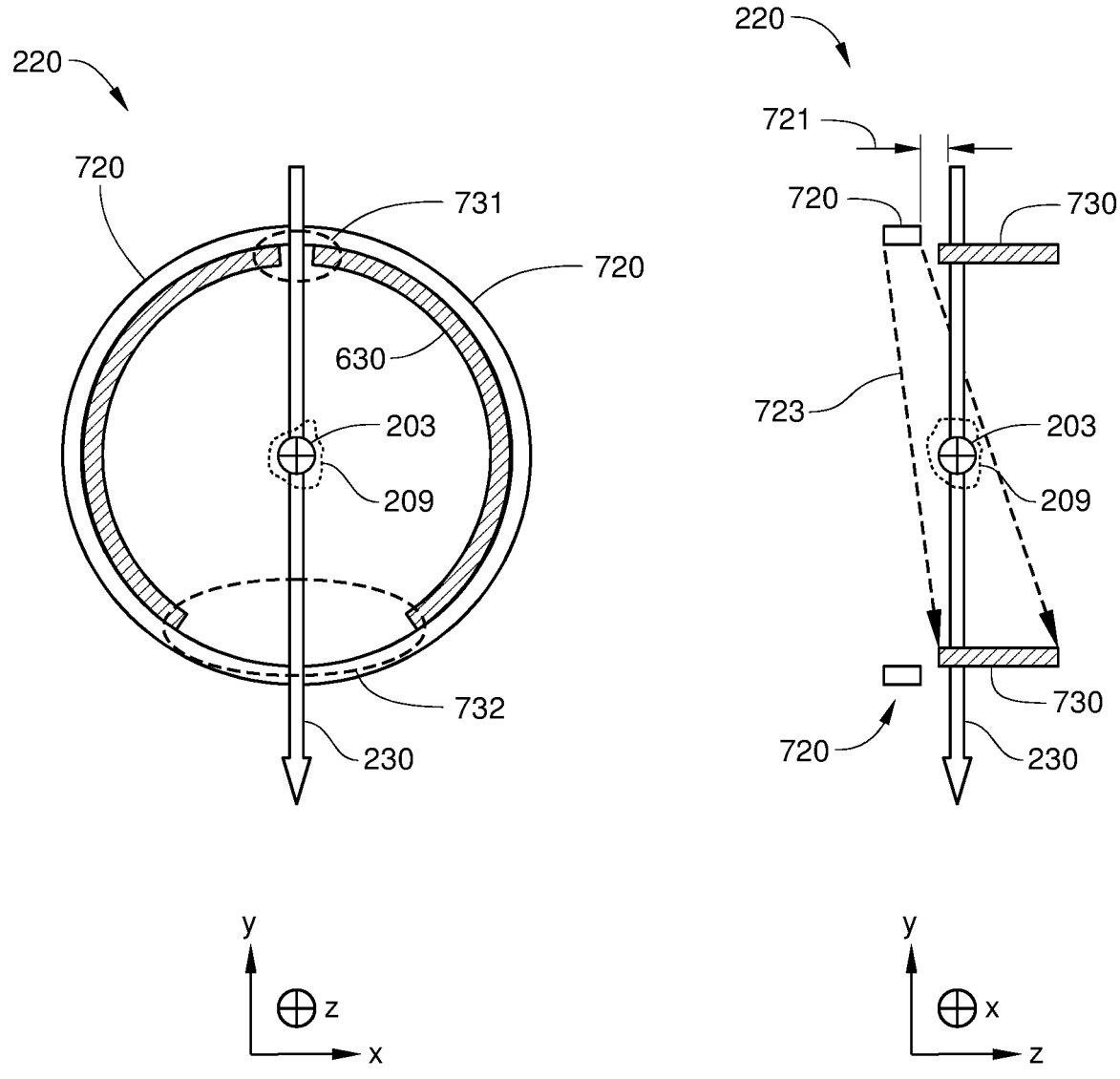
FIG. 7A is a schematic axial view of a CT imaging system and FIG. 7B is a schematic side view of the CT imaging system, according to an embodiment.

FIG. 3 schematically illustrates a digital volume 300 that is reconstructed based on a plurality of CT views (e.g., several hundred) acquired by CT imaging system 220 of FIG. 2, according to various embodiments. Digital volume 300 includes a plurality of voxels 301 (dashed lines) of anatomical image data, where each voxel 301 corresponds to a different location within digital volume 300. For clarity, only a single voxel 301 is shown in FIG. 3. Digital volume 300 corresponds to a 3D region that includes target volume 310. In FIG. 3, digital volume 300 is depicted as an 8×8×8 voxel cube, but in practice, digital volume 300 generally includes many more voxels, for example one or more orders of magnitude more than are shown in FIG. 3. Once digital volume 300 is reconstructed from a set of CT views, cross-sectional images of digital volume 300 can be generated at any location and in any of various planes, including the axial plane (which passes through patient anatomy from anterior to posterior, dividing the anatomy into superior and inferior sections), the coronal plane (which passes through patient anatomy from left to right and divides the anatomy into anterior and posterior sections), the sagittal plane (which passes through patient anatomy from anterior to posterior and divides the anatomy into left and right sections), and/or the oblique plane (which passes through patient anatomy at an angle to the axial, coronal, and/or sagittal planes).

For purposes of discussion, target volume 310 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by x-ray imaging of digital volume 300.

CT LINAC

FIG. 4A is a schematic axial (z-direction) view of CT imaging system 220 and FIG. 4B is a schematic side (x-direction) view of CT imaging system 220, according to an embodiment. For reference, treatment isocenter 203 is also indicated in FIGS. 4A and 4B. In the embodiment shown, CT imaging system 220 includes a distributed source assembly 420 and an arcuate X-ray imager 430 (cross-hatched), where each is positioned around treatment isocenter 203. Distributed source assembly 420 includes a plurality of x-ray sources 421, each of which is positioned to direct imaging x-rays through a region 403 of patient anatomy and towards a different portion of arcuate x-ray imager 430. As shown, region 403 generally includes treatment isocenter 203 and target volume 209.

In some embodiments, distributed source assembly 420 and arcuate x-ray imager 430 are mounted on a rotatable gantry, such as rotatable gantry 210 in FIG. 2. Therefore, in such embodiments, distributed source assembly 420 and arcuate x-ray imager 430 are rotated about treatment iso-center 203 simultaneously with other components of CT LINAC 100, such as LINAC 204 and EPID 205 of FIG. 2.

In the embodiment illustrated in FIGS. 4A and 4B, distributed source assembly 420 is depicted as a single contiguous ring-like structure or "source ring." In other embodiments, distributed source assembly 420 can include multiple adjacent segments of x-ray sources 421. Similarly, in the embodiment illustrated in FIGS. 4A and 4B, arcuate x-ray imager 430 is depicted as a single contiguous ring-like structure or "detector ring." In other embodiments, arcuate x-ray imager 430 can include multiple adjacent segments or sub-arrays (not shown) of x-ray detectors.

In operation, a different CT view of region 403 and target volume 209 is acquired for each x-ray source 421 included in distributed source assembly 420. More specifically, for each different CT view of region 403, a different x-ray source 421 directs imaging x-rays through region 403 towards a different portion of arcuate x-ray imager 430. Because each CT view of region 403 is generated based on imaging x-rays originating from an x-ray source 421 having a different position about treatment isocenter 203 and region 403, a complete set of CT views of region 403 can be acquired by x-ray imager 430 without rotating CT imaging system 220 about treatment isocenter 203. Instead, the complete set of CT views is acquired by selectively and rapidly generating imaging x-rays with different x-ray sources 421. By way of example, in FIGS. 4A and 4B, a single x-ray source 422 is shown directing imaging x-rays 423 towards a specific portion 433 of arcuate x-ray imager 430. Embodiments of a single x-ray source directing imaging x-rays towards a specific portion of an arcuate x-ray imager are described below in conjunction with FIGS. 5A-5B.

FIG. 5A is a schematic axial (z-direction) view of a single x-ray source 521 directing imaging x-rays 523 towards a specific portion 533 of an arcuate x-ray imager 530, and FIG. 5B is a schematic side (x-direction) view of x-ray source 521 directing imaging x-rays 523 towards specific portion 533 of arcuate x-ray imager 530, according to an embodiment. For reference, a patient 501, treatment isocenter 203, and target volume 209 are also indicated in FIGS. 5A and 5B. In the embodiment shown, x-ray source 521 directs imaging x-rays 523 with a fan angle 524 that encompasses the entire width of patient 501. In other embodiments, fan angle 524 is selected such that imaging x-rays 523 encompass the entire width of a particular region of interest or specific portion of the anatomy of patient 501, such as the head, the heart, or the like.

As noted previously, x-ray source 521 is one of a plurality of x-ray sources included in a distributed source assembly (such as distributed source assembly 420 in FIGS. 4A and 4B). In some embodiments, the distributed source assembly is substantially circular or otherwise arcuate in configuration, so that each x-ray source faces a different aspect of patient 501 and target volume 209. Unlike conventional CT x-ray sources, x-ray source 521 includes a nanotube-based, electron field emission emitter (or "cold cathode") instead of a thermionic emitter, which has a tungsten filament. Such a nanotube emitter can emit electrons at room temperature when driven by a suitable electric field, thereby enabling a large number of x-ray emitters to be disposed within a vacuum enclosure. Currently, nanotube emitters configured in a distributed source array can operate with a power of 10-15 kW or more. Further, unlike conventional CT x-ray sources, such nanotube emitters are not subject to periodic and expensive replacement due to thermal breakdown.

Arcuate x-ray imager 530 includes a two-dimensional array of x-ray detectors 531. Generally, the two-dimensional array includes a sufficient number of rows 532 of x-ray detectors 531 to axially (z-direction) span a targeted region of patient 501 without axial translation of x-ray source 521 and arcuate x-ray imager 530. In the embodiment illustrated in FIGS. 5A-5B, arcuate x-ray imager 530 includes four rows 532. In practice, arcuate x-ray imager 530 typically includes many more rows 532, for example, 256 rows, 320 rows, 640 rows, or more. Thus, the single CT view acquired by portion 533 of arcuate x-ray imager 530 that receives imaging x-rays 523 can span a significant portion of patient 501 in the axial direction.

Arcuate x-ray imager 530 can include a two-dimensional array of any technically feasible x-ray detectors, such as a glass substrate with a matrix or array of pixel detector elements formed thereon that each convert incident x-ray photons to electrical charge. For example, in some embodiments, arcuate x-ray imager 530 is configured as an indirect detector, in which a scintillator material in arcuate x-ray imager 530 is excited by incident x-rays and emits light that is detected by a plurality of photodiodes. Thus, in such embodiments, each x-ray detector 531 of arcuate x-ray imager 530 corresponds to a different photodiode. Each photodiode generates a signal (e.g., an accumulated voltage that is proportional to incident light intensity) for a different pixel of what will eventually become a digital image. An encoder included in arcuate x-ray imager 530 then interprets each of these voltages and assigns a value to each that is proportional to the voltage. Alternatively, in other embodiments arcuate Xx-ray imager 530 can be a direct detector. In a direct detector, incident x-ray photons are converted directly into charge in an amorphous selenium layer, and the resultant charge pattern therein is read out by suitable hardware, such as a thin-film transistor (TFT) array, an active-matrix array, microplasma line addressing, or the like. Since arcuate X-ray imager 530 includes a two-dimensional array of x-ray detectors, arcuate x-ray imager 530 is configured as the imager of a multiple-slice CT scanner, where each row 532 corresponds to a different CT slice acquisition.

As shown, when acquiring a particular CT view of patient 501, portion 533 of arcuate x-ray imager 530 receives imaging x-rays 523, while the majority of x-ray imager 530 does not. Further, when a set of CT views of patient 501 is acquired for a particular CT scan, a different portion 533 of arcuate x-ray imager 530 is associated with each different CT view of patient 501. However, the portion 533 for one CT view partially overlaps with a plurality of the portions 533 for other CT views. Thus, a specific x-ray detector 534 (cross-hatched) is generally included in a plurality of different portions 533 of arcuate X-ray imager 530.

It is noted that the above-described embodiments of CT LINAC 100 can provide highly temporally resolved images of patient anatomy with the high-contrast anatomical representation associated with a conventional CT. Thus, the region of patient anatomy that includes treatment isocenter 203 can be imaged during treatment delivery with high-quality images, thereby enabling new clinical workflows and highly conformal treatments, such as radiosurgery applications. In addition, the region of patient anatomy that includes treatment isocenter 203 can be imaged immediately prior to treatment delivery with CT-quality images, thereby improving the quality of an adaptive therapy plan of the day.

CT LINAC Alternative Configurations

In the embodiments of CT imaging system 220 illustrated above, each of a distributed source assembly and an arcuate x-ray imager is configured as a complete ring-like structure about the treatment isocenter of CT LINAC 100. In such embodiments, CT views of the patient anatomy can be acquired from all angles, and therefore CT image quality is maximized. Consequently, such embodiments are particularly useful for performing plan verification and adaptation. In other embodiments, a distributed source assembly and/or an arcuate x-ray imager of CT imaging system 220 is configured as an incomplete ring-like structure about the treatment isocenter and/or is movable relative to a treatment beam. Examples of such embodiments are described below.

FIG. 6 is a schematic axial (z-direction) view of CT imaging system 220, according to an embodiment. In the embodiment shown, CT imaging system 220 includes a distributed source assembly 620 that includes a plurality of x-ray sources (not shown) and is formed partially around treatment isocenter 203. CT imaging system 220 further includes an arcuate x-ray imager 630 (cross-hatched) that is also formed partially around treatment isocenter 203. In such embodiments, CT imaging system 220 can be employed for pre-planning imaging, because arcuate x-ray imager 630 can acquire CT views of target volume 209 from most viewing angles.

FIG. 7A is a schematic axial (z-direction) view of CT imaging system 220 and FIG. 7B is a schematic side (x-direction) view of CT imaging system 220, according to an embodiment. In the embodiment shown, CT imaging system 220 includes a distributed source assembly 720 that includes a plurality of x-ray sources (not shown) and forms a substantially complete source ring around treatment isocenter 203. CT imaging system 220 further includes an arcuate x-ray imager 730 (cross-hatched) that is formed partially around treatment isocenter 203. As shown, treatment beam 230 avoids distributed source assembly 720 due to an axial offset 721 between treatment beam 230 and distributed source assembly 720. By contrast, treatment beam 230 avoids arcuate X-ray imager 730 by passing through openings 731 and 732 of arcuate x-ray imager 730. Suitable openings 731 and 732 can be selected based on the geometry of CT imaging system 220, treatment beam 230, and target volume 209. In such embodiments, CT imaging system 220 can be employed for imaging of target volume 209 during treatment delivery using imaging x-rays 723.

Figure 8:
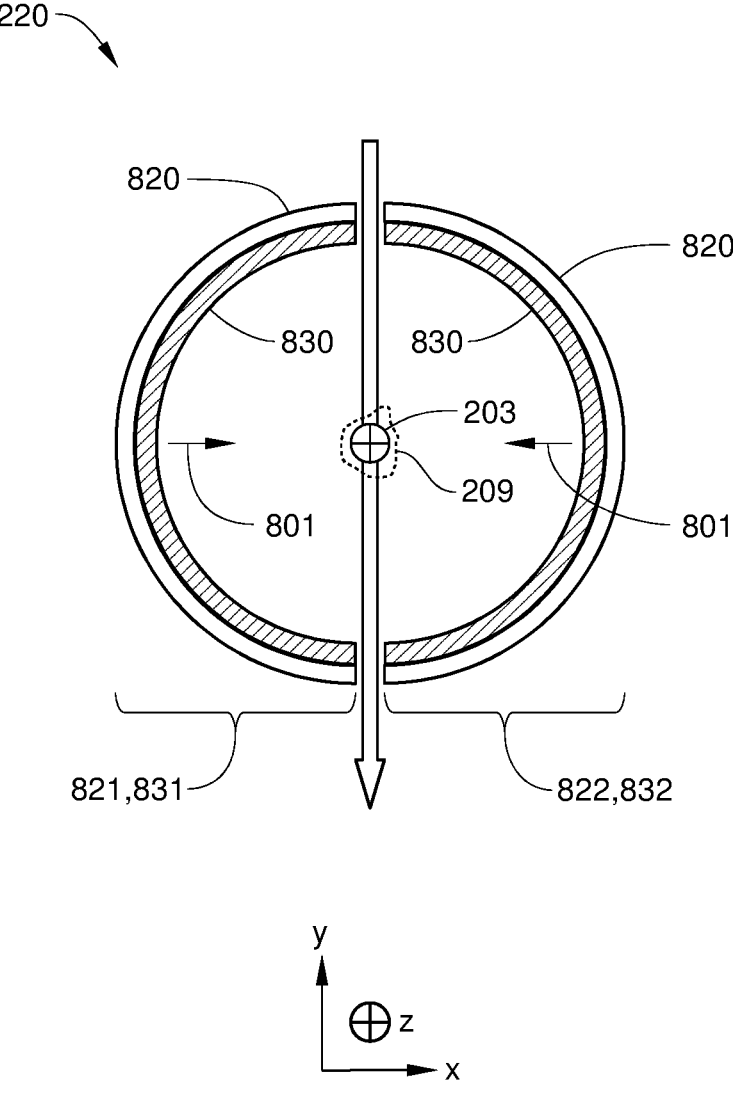
FIG. 8 is a schematic axial view of a CT imaging system, according to an embodiment.
Figure 9:
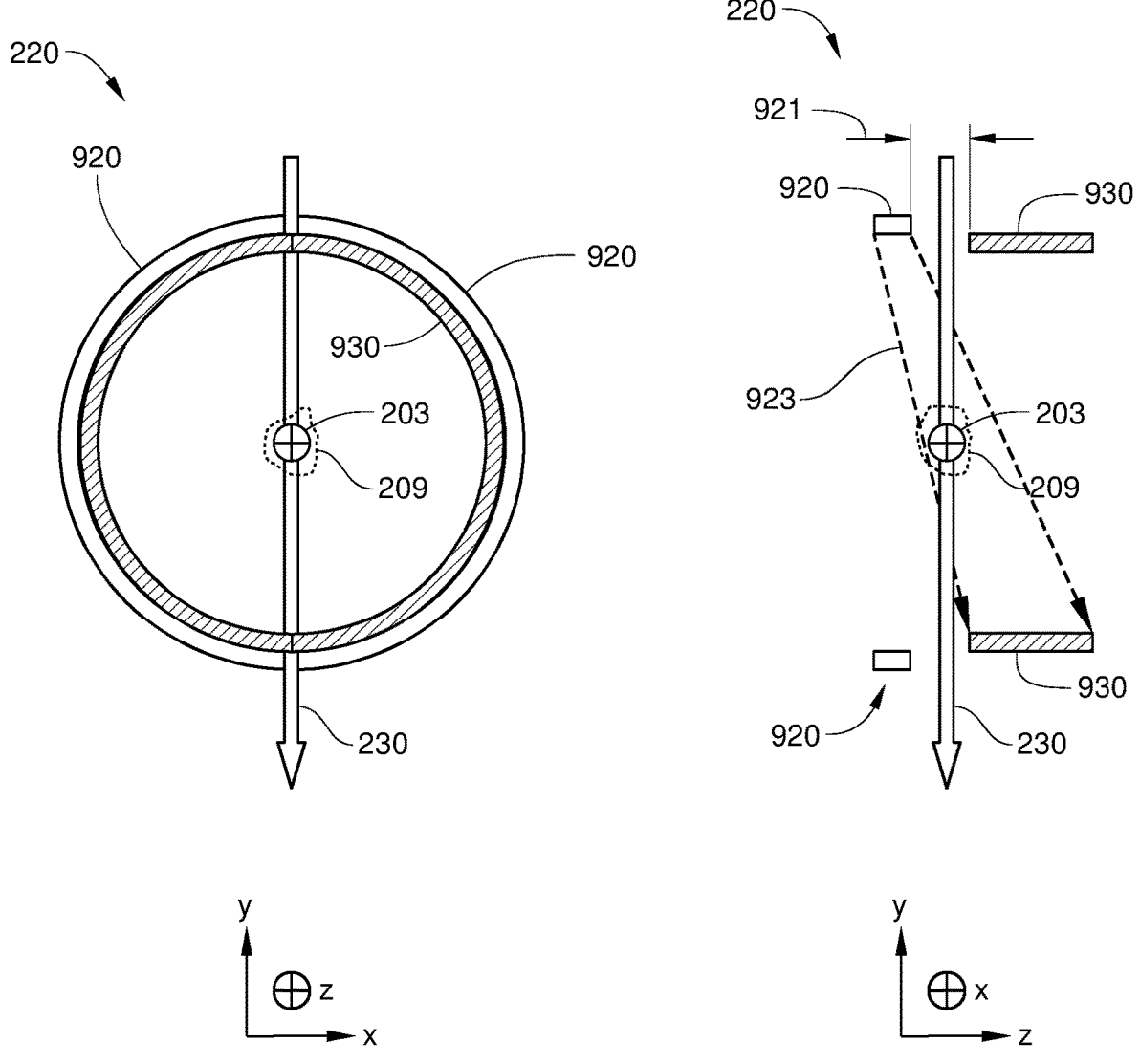
FIG. 9A is a schematic axial view of a CT imaging system and FIG. 9B is a schematic side view of the CT imaging system, according to an embodiment.

FIG. 8 is a schematic axial (z-direction) view of CT imaging system 220, according to an embodiment. In the embodiment shown, CT imaging system 220 includes a distributed source assembly 820 that includes a first source sub-assembly 821 and a second source sub-assembly 822 that can be separated horizontally (x-direction) as shown. First source sub-assembly 821 includes a plurality of x-ray sources (not shown) and is formed partially around treatment isocenter 203 (for example up to a 180-degree arc) and second source sub-assembly 822 also includes a plurality of x-ray sources (not shown) and is formed partially around treatment isocenter 203 (for example up to a 180-degree arc). Together, first source sub-assembly 821 and second source sub-assembly 822 form a nearly complete 360-degree arc around treatment isocenter 203 and target volume 209, and therefore can direct imaging x-rays (not shown) from most viewing angles. CT imaging system 220 further includes an arcuate x-ray imager 830 (cross-hatched) that includes a first detector sub-assembly 831 and a second detector sub-assembly 832 that can also be separated horizontally (x-direction) as shown. First detector sub-assembly 831 includes a plurality of x-ray detectors (not shown) and is formed partially around treatment isocenter 203 (for example up to a 180-degree arc) and second detector sub-assembly 832 also includes a plurality of x-ray detectors (not shown) and is formed partially around treatment isocenter 203 (for example up to a 180-degree arc). Together, first detector sub-assembly 831 and second detector sub-assembly 832 form a nearly complete 360-degree arc around treatment isocenter 203 and target volume 209, and therefore can acquire CT views of target volume from most viewing angles.

In the embodiment illustrated in FIG. 8, CT imaging system 220 can be employed for imaging of target volume 209 during treatment delivery, because distributed source assembly 820 and arcuate x-ray imager 830 do not interfere with treatment beam 230. In addition, in the embodiment illustrated in FIG. 8, CT imaging system 220 can be employed for pre-planning imaging, because distributed source assembly 820 and arcuate x-ray imager 830 can generate CT views of target volume 209 from most viewing angles. Further, in some embodiments, higher-quality imaging can be performed with CT imaging system 220 when treatment beam 230 is not being delivered. Specifically, first source sub-assembly 821 and second source sub-assembly 822 can be moved together to form a nearly complete 360-degree arc around target volume 209 and first detector sub-assembly 831 and second detector sub-assembly 832 can be moved together to form a nearly complete 360-degree arc around target volume 209. In such embodiments, CT imaging system 220 can be employed for pre-planning imaging and generate CT-quality imaging for treatment planning and/or day-of-treatment imaging, for example as part of a margin reduction daily online adaptive workflow.

FIG. 9A is a schematic axial (z-direction) view of CT imaging system 220 and FIG. 9B is a schematic side (x-direction) view of CT imaging system 220, according to an embodiment. In the embodiment shown, CT imaging system 220 includes a distributed source assembly 920 that includes a plurality of x-ray sources (not shown) and forms a substantially complete source ring around treatment iso-center 203. CT imaging system 220 further includes an arcuate x-ray imager 930 (cross-hatched) that forms a substantially complete detector ring around treatment isocenter 203. In the embodiment illustrated in FIGS. 9A and 9B, treatment beam 230 avoids distributed source assembly 920 due to an axial offset 921 between distributed source assembly 920 and arcuate x-ray imager 930. Specifically, treatment beam 230 can directed through axial offset 921 as shown. A suitable size for axial offset 921 can be selected based on the geometry of CT imaging system 220, treatment beam 230, and target volume 209. In such embodiments, CT imaging system 220 can be employed for imaging of target volume 209 during treatment delivery using imaging x-rays 923. Alternatively or additionally, in such embodiments, CT imaging system 220 can be employed for pre-planning imaging of target volume 209, because arcuate x-ray imager 930 can acquire CT views of target volume 209 from all viewing angles.

CT LINAC Operation

The above-described embodiments enable the integration of CT imaging of a treatment isocenter into a radiation therapy system, where the CT imaging can have the high temporal resolution (e.g., sub-second) and high soft tissue contrast associated with conventional CT scanners. As a result, in some embodiments, such onboard CT imaging can be employed by the radiation therapy system prior to treatment, for example for performing plan verification and/or adaptation. Further, in some embodiments, such onboard CT imaging can be employed by the radiation therapy system as real-time imaging during treatment, for example as part of IGRT and/or IMRT. Examples of such embodiments are described below in conjunction with FIGS. 10 and 11.

FIG. 10 sets forth a flowchart of a computer-implemented process 1000 for performing a CT scan of a region of patient anatomy, according to various embodiments. Computer-implemented process 1000 may include one or more operations, functions, or actions as illustrated by one or more of blocks 1001-1007. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 1000 is described in conjunction with CT LINAC 100 and FIGS. 1-9B, persons skilled in the art will understand that any suitably configured radiation therapy system is within the scope of the present embodiments.

In step 1001, CT LINAC 100 begins computer-implemented process 1000, which includes a CT scan of a region of patient anatomy, such as a region that includes target volume 209. The plurality of CT views of the region that are included in the CT scan can be used to reconstruct a digital volume of the region, such as digital volume 300. In some embodiments, computer-implemented process 1000 is performed to generate pre-treatment imaging, such as a treatment planning CT scan or a day-of-treatment CT scan for adaptive planning in adaptive radiotherapy (ART). In some embodiments, computer-implemented process 1000 is performed as part of real-time image-guided adaptive radiotherapy. In such embodiments, computer-implemented process 1000 may be performed periodically throughout delivery of treatment during a particular radiation treatment session or radiation treatment fraction. For example, computer-implemented process 1000 may be performed every 0.5 seconds during a radiation treatment session or fraction. Alternatively or additionally, computer-implemented process 1000 may be performed whenever rotatable gantry 210 reaches a particular predetermined position, such as every 5 degrees of rotation of rotatable gantry 210, or when LINAC 204 has reached a specified location and rotatable gantry 210 has briefly stopped for treatment delivery.

In embodiments in which CT imaging system 220 includes a distributed source assembly and/or x-ray imager that can be separated horizontally, CT LINAC 100 moves the separable sub-assemblies apart prior to step 1001 when computer-implemented process 1000 is performed to generate CT imaging during treatment delivery. Conversely, CT LINAC 100 moves the separable sub-assemblies together prior to step 1001 when computer-implemented process 1000 is performed to generate pre-treatment imaging, such as a treatment planning CT scan or a day-of-treatment CT scan. For example, in some embodiments, CT imaging system 220 may include distributed source assembly 820 (with first source sub-assembly 821 and second source sub-assembly 822 that can be separated horizontally) and/or arcuate x-ray imager 830 (with first detector sub-assembly 831 and second detector sub-assembly 832 that can be separated horizontally). In such embodiments, prior to step 1001, CT LINAC 100 either moves the sub-assemblies together or apart for the duration of computer-implemented method 1000.

In step 1002, CT LINAC 100 selects a specific x-ray source, such as x-ray source 421, from the distributed source assembly, such as distributed source assembly 420. In each iteration of step 1002, a different x-ray source is selected, so that each x-ray source is selected one time for a particular CT scan. In some embodiments, CT LINAC 100 selects an x-ray source that is adjacent to the x-ray source that was selected in the immediately preceding iteration of step 1002. In other embodiments, CT LINAC 100 selects an x-ray source that has a specified viewing angle relative to target volume 209. In such embodiments, the specified viewing angle is generally a different angle for each iteration of step 100.

In step 1003, CT LINAC 100 causes the selected x-ray source to direct imaging x-rays towards a particular portion of the x-ray imager of CT LINAC 100, such as x-ray imager 430. Generally, the imaging x-rays pass through target volume 209 and/or a region of patient anatomy that include target volume 209, so that a single CT view of target volume 209 and the surrounding region of patient anatomy can be acquired by the particular portion of the x-ray imager.

In step 1004, a portion of the x-ray imager of CT LINAC 100 acquires a CT view of target volume 209 and the surrounding region of patient anatomy in response to the selected source directing x-ray thereto. As noted previously, for each different x-ray source 421 of distributed source assembly 420, the portion of the x-ray imager of CT LINAC 100 that acquires a CT view includes a different set of detectors. Generally, each CT view acquired by the portion of the x-ray imager includes a plurality of slices—one slice for each row of detectors included in the x-ray imager.

In step 1005, CT LINAC 100 determines whether the CT scan is complete. If no, computer-implemented method 1000 returns to step 1002, and another x-ray source is selected; if yes, computer-implemented method 1000 proceeds to step 1006. In some embodiments, CT LINAC 100 determines the CT scan is complete when every x-ray source 421 in distributed source assembly 420 has directed imaging x-rays towards target volume 209 during computer-implemented method 1000. In other embodiments, CT LINAC 100 determines the CT scan is complete when every x-ray source 421 in a specific subset of the x-ray sources of distributed source assembly 420 has directed imaging x-rays towards target volume 209 during computer-implemented method 1000. For example, in one such embodiment, the specific subset of x-ray sources includes all x-ray sources 421 on one side target volume 209. In another such embodiment, the specific subset of x-ray sources includes a particular fraction of the x-ray sources 421 of distributed source assembly 420, such as every second x-ray source 421, every third x-ray source 421, every fourth x-ray source 421, or the like. In another such embodiment, the specific subset of x-ray sources includes all x-ray sources 421 included within a specified arc of distributed source assembly 420.

In step 1006, CT LINAC 100 reconstructs a digital volume based on the completed CT scan. In step 1007, CT LINAC 100 ends the CT scan.

Figure 11:
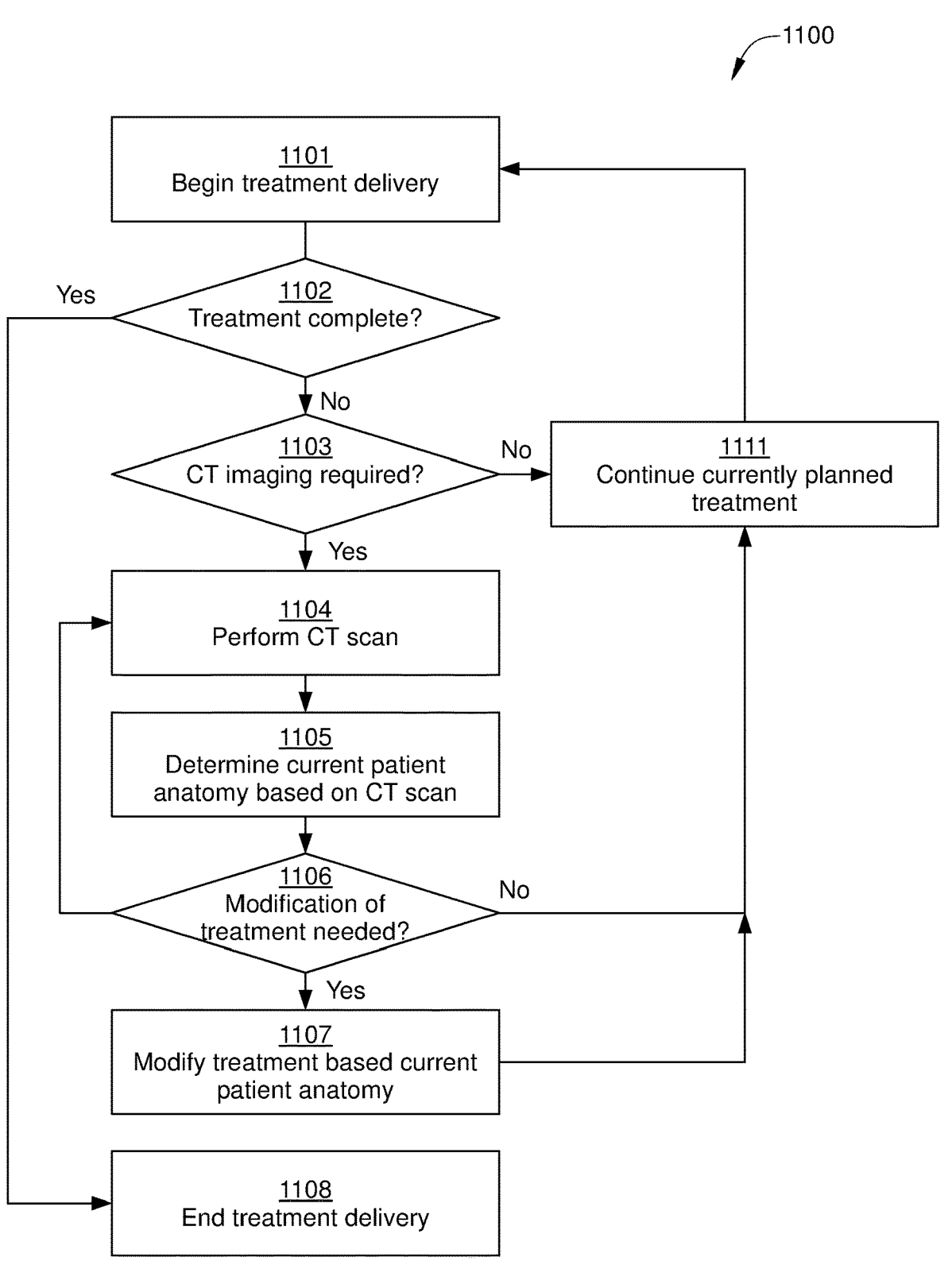
FIG. 11 sets forth a flowchart of a computer-implemented process 1100 for performing radiation therapy on a region of patient anatomy, according to various embodiments.

FIG. 11 sets forth a flowchart of a computer-implemented process 1100 for performing radiation therapy on a region of patient anatomy, according to various embodiments. Computer-implemented process 1100 may include one or more operations, functions, or actions as illustrated by one or more of blocks 1101-1111. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 1100 is described in conjunction with CT LINAC 100 and FIGS. 1-9B, persons skilled in the art will understand that any suitably configured radiation therapy system is within the scope of the present embodiments.

In step 1101, CT LINAC 100 begins computer-implemented process 1100, which includes the treatment and CT imaging of a region of patient anatomy, such as a region that includes target volume 209. In some embodiments, computer-implemented process 1100 is performed as part of an IGRT, IMRT, ART, or other imaging-related process. In step 1101, CT LINAC begins rotating rotatable gantry 210, for example at a specified rotational speed for delivery of treatment beam 230 to target volume 209. Since CT imaging system 220 and LINAC 204 are both mounted on rotatable gantry 210, CT imaging system 220 and LINAC 204 are statically coupled to each other and rotate together at the same rotational velocity about treatment isocenter 203. In step 1101, CT imaging system 220 also directs treatment beam 230 to target volume 209 as appropriate. In some embodiments, treatment beam 230 is directed to target volume 209 continuously. In some embodiments, treatment beam 230 is directed to target volume 209 in pulses. In some embodiments, treatment beam 230 is directed to target volume 209 for a time interval in which rotatable gantry 210 has stopped rotating.

In step 1102, CT LINAC system 100 determines whether the current treatment is complete. If yes, computer-implemented process 1100 proceeds to step 1108 and the treatment ends. If no, computer-implemented process 1100 proceeds to step 1103.

In step 1103, CT LINAC system 100 determines whether CT imaging is required at the current point in computer-implemented process 1100. If no, computer-implemented process 1100 proceeds to step 1111 and the treatment continues. If yes, computer-implemented process 1100 proceeds to step 1104. In some embodiments, such as in a real-time IGRT process, CT imaging of patient anatomy surrounding target volume 209 is performed periodically throughout computer-implemented process 1100, such as once every 0.5 seconds. Thus, such imaging provides real-time information regarding patient anatomy. Alternatively or additionally, in some embodiments, CT imaging of patient anatomy is performed whenever rotatable gantry 210 reaches a particular predetermined position, such as every 5 degrees of rotation of rotatable gantry 210. Thus, CT imaging of patient can be acquired immediately prior to when LINAC 204 directs treatment beam 230 to target volume 209 from a specified angle. Alternatively or additionally, in some embodiments, CT imaging of patient anatomy is performed whenever rotatable gantry 210 has reached a specified location and rotatable gantry 210 has briefly stopped for treatment delivery.

In step 1104, CT LINAC system 100 performs a CT scan of patient anatomy as described above in computer-implemented method 1000. In step 1105, CT LINAC system 100 determines current patient anatomy based on the CT scan performed in step 1104. For example, in some embodiments, a digital volume of the patient anatomy surrounding target volume 209 is reconstructed based on the plurality of CT views acquired in the CT scan of step 1104.

In step 1106, CT LINAC system 100 determines whether modification to the planned treatment is indicated. If no, computer-implemented process 1100 proceeds to step 1111 and the treatment continues. If yes, computer-implemented process 1100 proceeds to step 1107. In some embodiments, indications for modifying the planned treatment include a change in location of target volume 209 relative to treatment isocenter 203 and/or an organ at risk (OAR). For example, in such embodiments, when a current location of target volume 209 is determined to be greater than a threshold distance from a planned or expected location, CT LINAC system 100 determines that modification to the planned treatment is indicated. Alternatively or additionally, in some embodiments, indications for modifying the planned treatment include a change in location of an OAR relative to treatment isocenter 203 and/or target volume 209. Thus, in such embodiments, when a current location of a particular OAR is determined to be greater than a threshold distance from a planned or expected location relative to target volume 209 and/or treatment isocenter 203, CT LINAC system 100 determines that modification to the planned treatment is indicated.

In some embodiments, modification of the planned treatment can include aborting the current treatment and ending computer-implemented process 1100. For example, in some instances, the current patient anatomy may indicate loss of patient breath hold, excessive motion of the patient, or some other large change in body position of the patient. In such an instance, CT LINAC system 100 may determine that the change in body position is too great to be compensated for via real-time modifications to the delivery of treatment beam 230.

In step 1107, CT LINAC system 100 modifies the planned treatment or the currently modified treatment based on the current patient anatomy determined in step 1105. Thus, a real-time IGRT process is performed, in which sub-second temporal resolution of the CT scan provides immediate patient anatomy during the IGRT process.

Step 1111, CT LINAC system 100 continues the currently planned treatment. In some instances, the currently planned treatment is the originally planned treatment for the current radiation treatment session or radiation treatment fraction. In other instances, the currently planned treatment is a modified treatment that is determined based on the current patient anatomy determined in step 1105.

In sum, embodiments described herein provide a system that incorporates real-time CT imaging with a photon LINAC or other treatment beam radiation source. The embodiments enable best-quality CT imaging in the treatment isocenter immediately before each treatment fraction and/or during plan delivery. Thus, the embodiments can enable new clinical workflows and/or allow for highly conformal treatments, such as radiosurgery applications. These technical advantages provide one or more technological advancements over prior art approaches.

Example Computing Device

Figure 12:
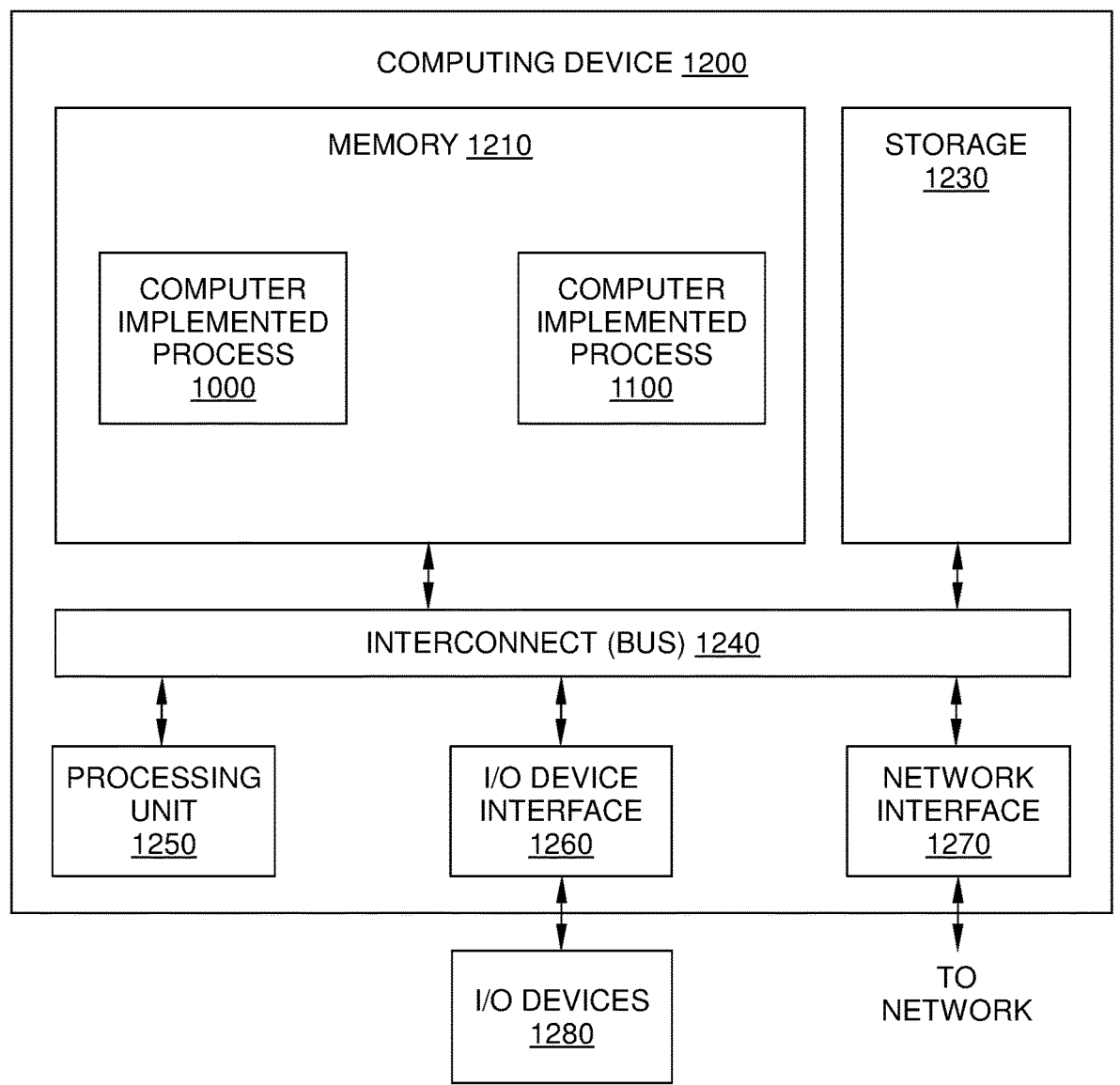
FIG. 12 is an illustration of a computing device configured to perform various embodiments.

FIG. 12 is an illustration of computing device 1200 configured to perform various embodiments of the present disclosure. For example, in some embodiments, computing device 1200 can be implemented as image acquisition and treatment control computer 106 and/or remote control console 120 in FIG. 1. Computing device 1200 may be a desktop computer, a laptop computer, a smart phone, or any other type of computing device suitable for practicing one or more embodiments of the present disclosure. In operation, computing device 1200 is configured to execute instructions associated with computer-implemented process 1000 and/or computer-implemented process 1100 as described herein. It is noted that the computing device described herein is illustrative and that any other technically feasible configurations fall within the scope of the present disclosure.

As shown, computing device 1200 includes, without limitation, an interconnect (bus) 1240 that connects a processing unit 1250, an input/output (I/O) device interface 1260 coupled to input/output (I/O) devices 1280, memory 1210, a storage 1230, and a network interface 1270. Processing unit 1250 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1250 may be any technically feasible hardware unit capable of processing data and/or executing software applications, including computer-implemented process 1000 and/or computer-implemented process 1100.

I/O devices 1280 may include devices capable of providing input, such as a keyboard, a mouse, a touch-sensitive screen, and so forth, as well as devices capable of providing output, such as a display device and the like. Additionally, I/O devices 1280 may include devices capable of both receiving input and providing output, such as a touchscreen, a universal serial bus (USB) port, and so forth. I/O devices 1280 may be configured to receive various types of input from an end-user of computing device 1200, and to also provide various types of output to the end-user of computing device 1200, such as displayed digital images or digital videos. In some embodiments, one or more of I/O devices 1280 are configured to couple computing device 1200 to a network.

Memory 1210 may include a random access memory (RAM) module, a flash memory unit, or any other type of memory unit or combination thereof. Processing unit 1250, I/O device interface 1260, and network interface 1270 are configured to read data from and write data to memory 1210. Memory 1210 includes various software programs that can be executed by processor 1250 and application data associated with said software programs, including computer-implemented process 1000 and/or computer-implemented process 1100.

Example Computer Program Product

Figure 13:
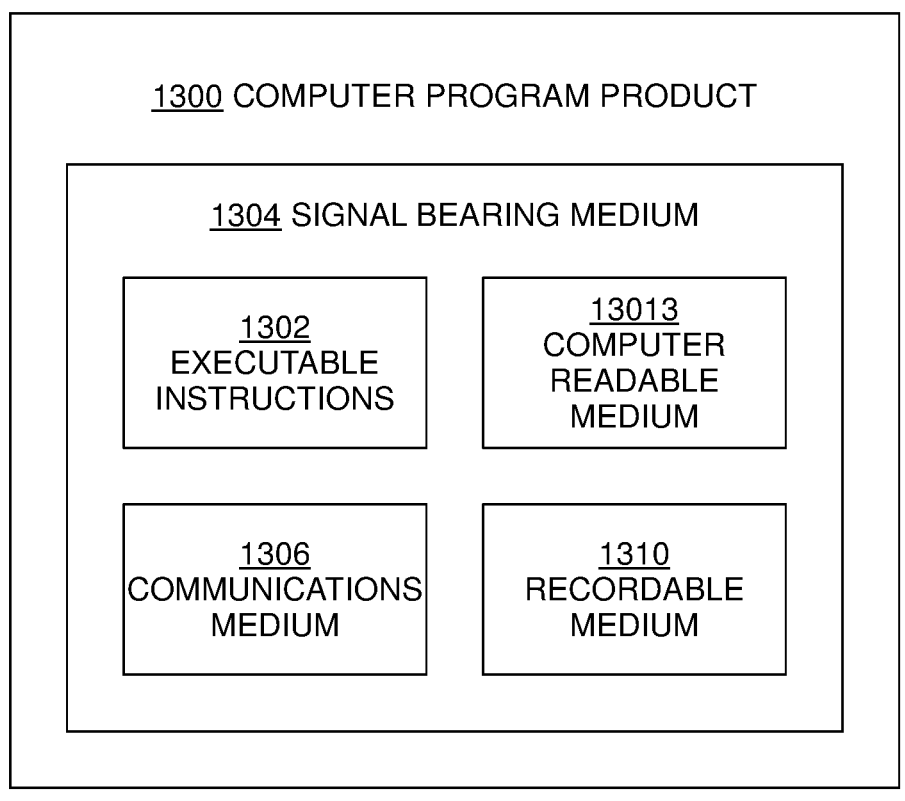
FIG. 13 is a block diagram of an illustrative embodiment of a computer program product for implementing one or more embodiments.

FIG. 13 is a block diagram of an illustrative embodiment of a computer program product 1300 for implementing a method for segmenting an image, according to one or more embodiments of the present disclosure. Computer program product 1300 may include a signal bearing medium 1304. Signal bearing medium 1304 may include one or more sets of executable instructions 1302 that, when executed by, for example, a processor of a computing device, may provide at least the functionality described above with respect to FIGS. 1-12.

In some implementations, signal bearing medium 1304 may encompass a non-transitory computer readable medium 1308, such as, but not limited to, a hard disk drive, a Compact Disc (CD), a Digital Video Disk (DVD), a digital tape, memory, etc. In some implementations, signal bearing medium 1304 may encompass a recordable medium 1310, such as, but not limited to, memory, read/write (R/W) CDs, R/W DVDs, etc. In some implementations, signal bearing medium 1304 may encompass a communications medium 1306, such as, but not limited to, a digital and/or an analog communication medium (e.g., a fiber optic cable, a waveguide, a wired communications link, a wireless communication link, etc.). Computer program product 1300 may be recorded on non-transitory computer readable medium 1308 or another similar recordable medium 1310.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. Throughout the present disclosure, the terms "first," "second," "third," etc. do not denote any order of importance, but are rather used to distinguish one element from another. Independent of the grammatical term usage, individuals with male, female, or other gender identities are included within the term.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A radiation treatment system comprising:
   a radiation delivery system that includes:
      a rotatable gantry that is coupled to a static portion of the radiation treatment system; and
      a radiation source that directs treatment radiation to a target volume and is mounted on the rotatable gantry for rotation about the target volume; and
   a computed tomography (CT) imaging system that generates portions of a CT scan of a region of patient anatomy that includes the target volume, wherein the CT imaging system includes:
      an arcuate array of x-ray detectors; and
      an array of x-ray sources positioned around the target volume, wherein for each portion of the CT scan, a different x-ray source in the array of x-ray sources is oriented to direct imaging x-rays towards a different portion of the arcuate array of x-ray detectors.

2. The radiation treatment system of claim 1, wherein each portion of the CT scan comprises a CT view of the region of patient anatomy.

3. The radiation treatment system of claim 1, wherein each x-ray source in the array of x-ray sources is oriented so that at least a portion of the imaging x-rays directed towards the different portion of the arcuate x-ray detector passes through an isocenter of the radiation treatment system.

4. The radiation treatment system of claim 1, wherein each x-ray source in the array of x-ray sources directs the imaging x-rays towards the different portion with a fan angle that spans at least the target volume.

5. The radiation treatment system of claim 1, wherein each x-ray source in the array of x-ray sources comprises a field-emission nanotube-based x-ray tube.

6. The radiation treatment system of claim 1, wherein the arcuate array of x-ray detectors includes a plurality of solid-state x-ray detectors.

7. The radiation treatment system of claim 1, wherein the arcuate array of x-ray detectors includes a two-dimensional array of solid-state x-ray detectors.

8. The radiation treatment system of claim 1, wherein the array of x-ray sources includes a first source that directs imaging x-rays towards a first portion of the arcuate array of x-ray detectors and a second source that directs imaging x-rays towards a second portion of the arcuate array of x-ray detectors, wherein the first portion of the detector array includes at least one detector that is not included in the second portion of the detector array.

9. The radiation treatment system of claim 8, wherein the first portion of the detector array overlaps with the second portion of the detector array.

10. The radiation treatment system of claim 1, wherein the array of x-ray sources includes a first source that directs imaging x-rays towards a first portion of the arcuate array of x-ray detectors and a second source that directs imaging x-rays towards a second portion of the arcuate array of x-ray detectors, wherein the first portion of the detector array includes at least a two-dimensional group of detectors that are not included in the second portion of the detector array.

11. The radiation treatment system of claim 1, wherein the arcuate array of x-ray detectors, the array of x-ray sources, and the radiation source that is configured to direct treatment radiation to the target volume rotate about a treatment isocenter of the radiation treatment system at a first rotational velocity.

12. The radiation treatment system of claim 1, wherein the arcuate array of x-ray detectors, the array of x-ray sources, and the radiation source that is configured to direct treatment radiation to the target volume are mounted on the rotatable gantry.

13. The radiation treatment system of claim 1, wherein the radiation source directs the treatment radiation to the target volume between a first sub-assembly of the array of x-ray sources and a second sub-assembly of the array of x-ray sources.

14. The radiation treatment system of claim 1, wherein the radiation source directs the treatment radiation to the target volume between a first sub-assembly of the arcuate array of x-ray detectors and a second sub-assembly of the sub-assembly of the arcuate array of x-ray detectors.

15. The radiation treatment system of claim 1, wherein the radiation source directs the treatment radiation to the target volume via an offset between the array of x-ray sources and the arcuate array of x-ray detectors.

16. The radiation treatment system of claim 1, wherein the radiation source directs the treatment radiation to the target volume via at least one opening in the arcuate array of x-ray detectors.

17. A computer-implemented method of imaging a target volume in a patient anatomy, the method comprising:
   selecting a first source in an array of x-ray sources that are positioned around the target volume;
   acquiring a first portion of a computed tomography (CT) scan with a first portion of a detector array that receives imaging x-rays from the first source in the array of x-ray sources;
   after acquiring the first portion of the CT scan:
      selecting a second source in the array of x-ray sources; and
      acquiring a second portion of the CT scan with a second portion of the detector array that receives imaging x-rays from the second source in the array of x-ray sources; and
   based on the first portion of the CT scan and the second portion of the CT scan, reconstructing a digital volume of a region of patient anatomy that includes the target volume.

18. The computer-implemented method of claim 17, further comprising, after reconstructing the digital volume of the region of patient anatomy, directing a treatment radiation beam to the target volume.

19. The computer-implemented method of claim 18, further comprising directing the treatment radiation beam based at least in part on the digital volume of the region.

20. The computer-implemented method of claim 18, further comprising, prior to directing the treatment radiation beam to the target volume, determining a current location of one of the target volume or an organ at risk based on the digital volume of the region.

21. The computer-implemented method of claim 17, further comprising rotating the first source, the second source, and a source for the treatment radiation beam at a first rotational velocity about a treatment isocenter of the radiation treatment system while directing the treatment radiation beam to the target volume.

\* \* \* \* \*